US006869940B2

United States Patent
Ogata et al.

(10) Patent No.: US 6,869,940 B2
(45) Date of Patent: Mar. 22, 2005

(54) MALIGNANT TUMOR METASTASIS INHIBITORS

(75) Inventors: Etsuro Ogata, Tokyo (JP); Kyoji Ikeda, Aichi (JP); Koichi Endo, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 99 days.

(21) Appl. No.: 10/135,846

(22) Filed: May 1, 2002

(65) Prior Publication Data

US 2002/0198182 A1 Dec. 26, 2002

Related U.S. Application Data

(63) Continuation-in-part of application No. 09/091,185, filed as application No. PCT/JP96/03874 on Dec. 27, 1996, now Pat. No. 6,566,351.

(30) Foreign Application Priority Data

Dec. 28, 1995 (JP) .............................................. 7-354288

(51) Int. Cl.$^7$ .............................................. A61K 31/59
(52) U.S. Cl. ...................................................... 514/167
(58) Field of Search ........................................ 514/167

(56) References Cited

U.S. PATENT DOCUMENTS 6,566,351 B1 * 5/2003 Ogata et al. ................. 514/167

FOREIGN PATENT DOCUMENTS

| EP | 0 387 077 A1 | 9/1990 |
| WO | WO 91/00855 A1 | 1/1991 |
| WO | WO 94/14766 A1 | 7/1994 |
| WO | WO 95/27697 A1 | 10/1995 |
| WO | WO 95/28162 A1 | 10/1995 |

OTHER PUBLICATIONS

Skowronsky et al., Endocrinology (1995), 136(1), 20–6 Abstract only.*
Abe, et al. "A novel vitamin d3 analog, 22–oxa–1,25–dihydroxyvitamin D3, Inhibits The Growth Of Human Breast Cancer In Vitro And In Vivo", Endocrinology, (1991), 129(2): pp. 832–837, Abstract.

Franceschi, et al, "Regulation of Cellular Adhesion and Fibronectin Synthesis by 1a,25–dihydroxyvitamin $D_3$", Journal of Biological Chemistry (19870, 262(9): pp. 4165–4171.
Oikawa et al, "Antitumor Effect of 22–oxa–1a,25–dihydroxyvitamin $D_3$, A Potent Angiogenesis Inhibitor, On Rat Mammery Tumor Induced by 7,12–dimethylnez[a]anthracene" Anti–Cancer (1991), 2: pp. 475–480.
Young, et al, "Treating Tumor–Bearing Mice With Vitamin $D_3$ Diminishes Tumor–Induced Myelopoiesis And Associated Immunosuppression, And Reduces Tumor Metastasis And Recurrence" Cancer Immunol Innunother (1995) 41,: pp. 37–45.
Hamada et al, "Novel vitamin $D_3$ Analogs And Their Potential For Inhibiting Cancer Cell Growth" Drugs of the Future (1993) 18(11):1057–1061.

* cited by examiner

*Primary Examiner*—Rebecca Cook
(74) *Attorney, Agent, or Firm*—Browdy and Neimark, P.L.L.C.

(57) ABSTRACT

A method for inhibiting bone metastasis of a malignant tumor in a patient who has a cancer excluding breast cancer comprises administering to said patient an effective amount of a compound of the formula (III):

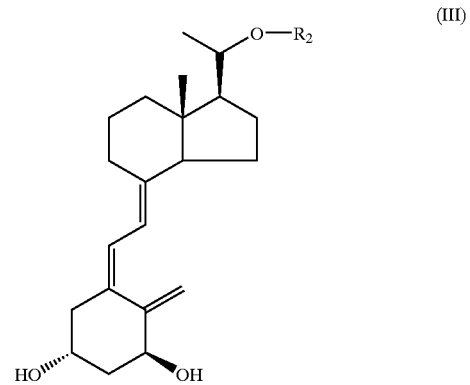

wherein $R_2$ represents a C1–C10 alkyl group substituted by one or more hydroxyl groups is provided.

3 Claims, 7 Drawing Sheets

NORMAL  20 DAYS AFTER TRANSPLANTATION

Fig. 4

VEHICLE  20 DAYS AFTER TRANSPLANTATION

Fig. 5

OCT    20 DAYS AFTER TRANSPLANTATION

Fig. 6

NORMAL    DAY 11

Fig. 7

VEHICLE    DAY 11

Fig. 8

OCT    DAY 11

Fig. 9

NORMAL   DAY 22

Fig. 10

VEHICLE   DAY 22

Fig. 11

OCT        DAY 22

Fig. 12

NORMAL     DAY 29

Fig. 13

VEHICLE    DAY 29

Fig. 14

OCT    DAY 29

MALIGNANT TUMOR METASTASIS INHIBITORS

CROSS-REFERENCED TO RELATED APPLICATIONS

The present invention is a continuation-in-part of Ser. No. 09/091,185, filed Jun. 10, 1998, now U.S. Pat. No. 6,566,351 which is a 371 of PCT/JP96/03874 filed Dec. 27, 1996, the entire contents of which are hereby incorporated by reference.

TECHNICAL FIELD

The present invention relates to malignant tumor metastasis inhibitors. More specifically, it relates to malignant tumor metastasis inhibitors containing an active vitamin D or a derivative thereof as an active ingredient.

BACKGROUND ART

The cure rate of malignant tumors is more and more increasing by early diagnosis and progress in therapies, but metastases of malignant tumors are often beyond current therapies and pose one of the important medical problems. At present, chemotherapies are used to arrest metastases following removal of tumors with unsatisfactory results, so that it would be desirable to develop more effective inhibitors against malignant tumor metastases.

Bone tissues are one of the most favored sites of metastases of malignant tumors, as a report shows that bone metastases occurred in about 30% of all the cancer cases from autopsy. Among malignant tumors, cancers of the lung, breast, prostate or the like are particularly known to be likely to metastasize to bone.

Vitamin D compounds are known to show a wide variety of physiological activities such as calcium metabolism regulation, growth inhibition or differentiation-inducing of tumor cells or the like, and immunoregulation. Vitamin D derivatives having an oxygen atom at the 22-position, which are particularly preferred compounds as malignant tumor metastasis inhibitors of the present invention, are known to have very few side effects commonly associated with this type of vitamin D compound. These compounds have been known to induce hypercalcemia, and they have been reported to be effective for psoriasis, secondary hyperparathyroidism or the like (for example, see JP No. 183534A/1988, JP No. 86382/1994, etc.). They are also known to have antitumor effects, but have not been reported yet to show inhibitory effects against metastases of malignant tumors.

It is an object of the present invention to provide metastasis inhibitors, malignant tumors and particularly pharmaceutical agents for inhibiting bone metastases of malignant tumors.

DISCLOSURE OF THE INVENTION

As a result of extensive research of malignant tumor metastasis inhibitors, it has been found that vitamin D derivatives of the general formula (I):

wherein $R_1$ represents $-O-R_2$, $-S-R_2$, $-CH_2-R_2$ or $-CH=R_2$ where $R_2$ represents a $C_1-C_{10}$ chain hydrocarbon group which may be substituted by one or more hydroxyl groups, and $R_3$ represents a hydrogen atom or a hydroxyl group are effective as metastasis inhibitors for malignant tumors, particularly as inhibitors against bone metastases of malignant tumors, and thus accomplished the present invention.

Therefore, the present invention relates to malignant tumor metastasis inhibitors containing a compound of the general formula (I):

wherein $R_1$ represents $-O-R_2$, $-S-R_2$, $-CH_2-R_2$ or $-CH=R_2$ where $R_2$ represents a $C_1-C_{10}$ chain hydrocarbon group which may be substituted by one or more hydroxyl groups, and $R_3$ represents a hydrogen atom or a hydroxyl group, as an active ingredient.

These compounds are particularly useful in preventing bone metastasis of a malignant tumor in patients who have cancers other than breast cancer.

BEST MODE FOR CARRYING OUT THE INVENTION

The compound of the general formula (I) is preferably represented by the general formula (II):

(II)

wherein $R_4$ represents $-O-R_2$ or $-CH_2-R_2$ where $R_2$ represents a $C_1-C_{10}$ chain hydrocarbon group which may be substituted by one or more hydroxyl groups, more preferably represented by the general formula (III):

(III)

wherein $R_2$ has the same meaning as defined above. Still preferably, $R_2$ is a $C_1-C_{10}$ alkyl group substituted by one or more hydroxyl groups. Most preferably, a malignant tumor metastasis inhibitor of the present invention is a compound of the formula (IV):

(IV)

In addition to the compound of the formula (IV), the compound of the general formula (I) preferably includes the following specific examples:

the compound of the formula (V): 1α(OH) vitamin $D_3$:

(V)

the compound of the formula (VI), 1α, 25(OH)$_2$ vitamin D$_3$:

the compound of the formula (VII), 1α, 24R(OH)$_2$ vitamin D$_3$:

the compound of the formula (VIII), EB1089:

the compound of the formula (IX), KH1060:

Another preferred example is the compound of the formula (X), MC903:

Vitamin D derivatives of the present invention are known compounds, as described in JP74656A/1991, WO94/14766, WO95/27697, JP506965A/1992, JP503669A/1992, for example.

As used herein, the term "$C_1$–$C_{10}$ chain hydrocarbon group" may be straight or branched and may contain one or more unsaturated bonds such as a double or a triple bond. The unsaturated bond is preferably a double bond. The $C_1$–$C_{10}$ chain hydrocarbon group preferably contains no unsaturated bonds or only one double bond thereon.

The $C_1$–$C_{10}$ chain hydrocarbon group moiety with no unsaturated bonds includes, for example, methyl, ethyl, n-propyl, i-propyl, n-butyl, i-butyl, s-butyl and t-butyl groups as well as pentyl, hexyl, heptyl, octyl, nonyl and decanyl groups, preferably 3-methylbutyl, 3-ethylpentyl, 4-methylpentyl, 3-(n-propyl)hexyl, 4-ethylhexyl, 5-methylhexyl, 6-methylheptyl, 5-ethylheptyl and 4-(n-propyl)heptyl groups, more preferably, 3-methylbutyl, 3-ethylpentyl, 4-methylpentyl and 4-ethylhexyl groups, most preferably 3-methylbutyl group.

The chain hydrocarbon group may or may not be substituted by one or more hydroxyl groups, and in the former case, the number of the hydroxyl groups is, for example, one, two or three, preferably one or two, more preferably one.

Examples of the $C_1$–$C_{10}$ alkyl group substituted by one or more hydroxyl groups include 3-hydroxy-3-methylbutyl, 2-hydroxy-3-methylbutyl, 4-hydroxy-3-methylbutyl, 2,3-dihydroxy-3-methylbutyl, 2,4-dihydroxy-3-methylbutyl, 3,4-dihydroxy-3-methylbutyl, 3-hydroxy-3-ethylpentyl, 2-hydroxy-3-ethylpentyl, 4-hydroxy-3-ethylpentyl, 2,3-dihydroxy-3-ethylpentyl, 2,4-dihydroxy-3-ethylpentyl, 3,4-dihydroxy-3-ethylpentyl, 4-hydroxy-4-methylpentyl, 3-hydroxy-4-methylpentyl, 5-hydroxy-4-methylpentyl, 3,4-dihydroxy-4-methylpentyl, 3,5-dihydroxy-4-methylpentyl, 4,5-dihydroxy-4-methylpentyl, 3-hydroxy-3-(n-propyl) hexyl, 4-hydroxy-3-(n-propyl) hexyl, 2-hydroxy-3-(n-propyl)hexyl, 2,3-dihydroxy-3-(n-propyl) hexyl, 3,4-dihydroxy-3-(n-propyl) hexyl, 2,4-dihydroxy-3-(n-propyl) hexyl, 3-hydroxy-4-ethylhexyl, 4-hydroxy-4-ethylhexyl, 5-hydroxy-4-ethylhexyl, 3,4-dihydroxy-4-ethylhexyl, 3,5-dihydroxy-4-ethylhexyl, 4,5-dihydroxy-4-ethylhexyl, 4-hydroxy-5-methylhexyl, 5-hydroxy-5-methylhexyl, 6-hydroxy-5-methylhexyl, 4,5-dihydroxy-5-methylhexyl, 4,6-dihydroxy-5-methylhexyl, 5,6-dihydroxy-5-methylhexyl, 5-hydroxy-6-methylheptyl, 6-hydroxy-6-methylhexyl, 7-hydroxy-6-methylheptyl, 5,6-dihydroxy-6-methylhexyl, 5,7-dihydroxy-6-methylheptyl, 6,7-dihydroxy-6-methylhexyl, 4-hydroxy-5-ethylheptyl, 5-hydroxy-5-ethylheptyl, 6-hydroxy-5-ethylheptyl, 4,5-dihydroxy-5-ethylheptyl, 4,6-dihydroxy-5-ethylheptyl, 5,6-dihydroxy-5-ethylheptyl, 3-hydroxy-4-(n-propyl)heptyl, 4-hydroxy-4-(n-propyl)heptyl, 5-hydroxy-4-(n-propyl) heptyl, 3,4-dihydroxy-4-(n-propyl)heptyl, 3,5-dihydroxy-4-(n-propyl)heptyl and 4,5-dihydroxy-4-(n-propyl)heptyl groups, preferably 3-hydroxy-3-methylbutyl, 2-hydroxy-3-methylbutyl, 2,3-dihydroxy-3-methylbutyl, 3,4-dihydroxy-3-methylbutyl, 3-hydroxy-3-ethylpentyl, 2,3-dihydroxy-3-ethylpentyl, 3,4-dihydroxy-3-ethylpentyl, 4-hydroxy-4-methylpentyl, 3,4-dihydroxy-4-methylbutyl, 4,5-dihydroxy-4-methylpentyl and 4-hydroxy-4-ethylhexyl groups, more preferably 3-hydroxy-3-methylbutyl, 3-hydroxy-3-ethylpentyl and 4-hydroxy-4-methylpentyl groups, most preferably 3-hydroxy-3-methylbutyl group.

Examples of the chain hydrocarbon group containing one or more unsaturated bonds include the above-mentioned hydrocarbon groups wherein one or more, preferably one bond, is an unsaturated bond, preferably double bond. Particularly preferred examples of the chain hydrocarbon group containing one or more unsaturated bonds include =CH—CH=CH—CH(CH$_2$CH$_3$)$_2$ and those further having hydroxy substituent(s) include =CH—CH=CH—CH(CH$_2$CH$_3$)$_2$OH.

In the general formula (I), R$_3$ is more preferably a hydroxyl group.

In addition to the compound of the general formula (I) as an active ingredient, the malignant tumor metastasis inhibitors of the present invention may contain pharmaceutically acceptable carriers including excipients and auxiliaries which facilitate formulation of said active compound.

Excipients include, but are not limited to, sugars such as lactose, sucrose, mannitol and sorbitol; celluloses; and/or fillers such as calcium phosphate.

Auxiliaries such as binders, rheology modulators, lubricants, and stabilizers may be added according to the necessity.

The dosage form of the agents of the present invention includes formulations for oral administration which are prepared by conventional formulation techniques of vitamin D compounds and formulations for parenteral administration, e.g. solutions such as injections based on an aqueous solvent, non-aggressive formulations such as collunaria, and formulations for external administration such as creams, ointments, but preferably formulations for oral administration and injections.

The malignant tumor metastasis inhibitors of the present invention can be administered to arrest further spread of a metastasis which has already occurred at the time of diagnosis of a cancer or can be prophylactically administered even in case of an early cancer which has not been metastasized yet. They can also be administered to prevent metastases following surgery or radiation therapy or to arrest micrometastases. The malignant tumor metastasis inhibitors of the present invention may be applied to any type of malignant tumors excluding breast cancer, but they are particularly effective against metastases of cancers of the lung and prostate, especially to bone.

The pharmaceutical agents of the present invention are preferably systemically administered by an oral route or as an injection, but may also be topically administered by an external route or the like.

The dosage of the vitamin D derivatives of the present invention will vary depending on the age, sex, condition or other factors of the patient, but usually ranges from 0.01 to 1000 μg, preferably 0.1 to 100 μg, especially 1 to 20 μg per day. The frequency of administration is not specifically limited, e.g. said dosage may be administered in a single dose or in divided doses of up to about three times daily.

EXAMPLE

The following example illustrates the present invention more in detail. In this example, 22-oxa-1α, 25-dihydroxyvitamin D$_3$ (OCT) of the formula (IV):

(IV)

was used as an active ingredient.

Example 1

Experiment on Bone Metastasis Mice

Preventive effects of OCT on bone metastases were studied using a bone metastasis model prepared with Hara cells derived from human lung cancer.

A test of preventive effects of OCT on bone metastases of Hara cells was started on the 20th day after 5×10$^5$ Hara cells were transplanted into the heart of nude mice, at which time the body weight of the animals began to slightly decrease but neither rise in Ca nor clear bone metastasis image on soft X-rays was observed. On that day, the animals were grouped by body weight, and a vehicle (n=9) or 1 μg/kg of OCT (n=9) was orally administered to each animal 4 to 5 times per week for six weeks (29 times in total). At different instants during the administration period, the body weight and Ca level in blood were measured and soft X-ray photographs were taken.

Figure 1:
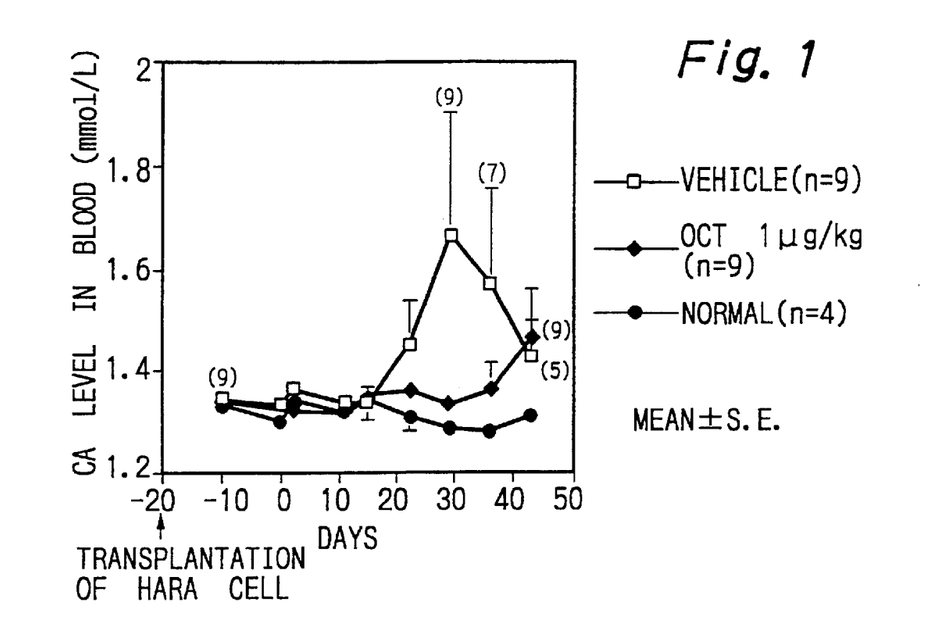
FIG. 1 shows Ca levels in blood of bone metastasis model mice.

FIG. 1 shows changes in Ca level in blood of the tested animals in function of time. The tested animals of the vehicle group (n=9) showed Ca levels in blood of 1.34±0.03 mM on the first day of the test, then 1.46±0.25 mM after 15 doses on the 22nd day after starting the test, and 1.67±0.7 mM after 20 doses on the 29th day after starting the test. In contrast, the group treated with 1 μg/kg of OCT (n=9) showed Ca levels of 1.32±0.04, 1.37±0.04 and 1.34±0.16 mM, respectively, indicating that OCT has a tendency to suppress the rise in Ca level in blood. Age-matched normal mice with no Hara cells transplanted (normal in FIG. 1; n=4) showed Ca levels in blood of 1.31±0.01, 1.32±0.05 and 1.29±0.01 mM, respectively.

Figure 2:
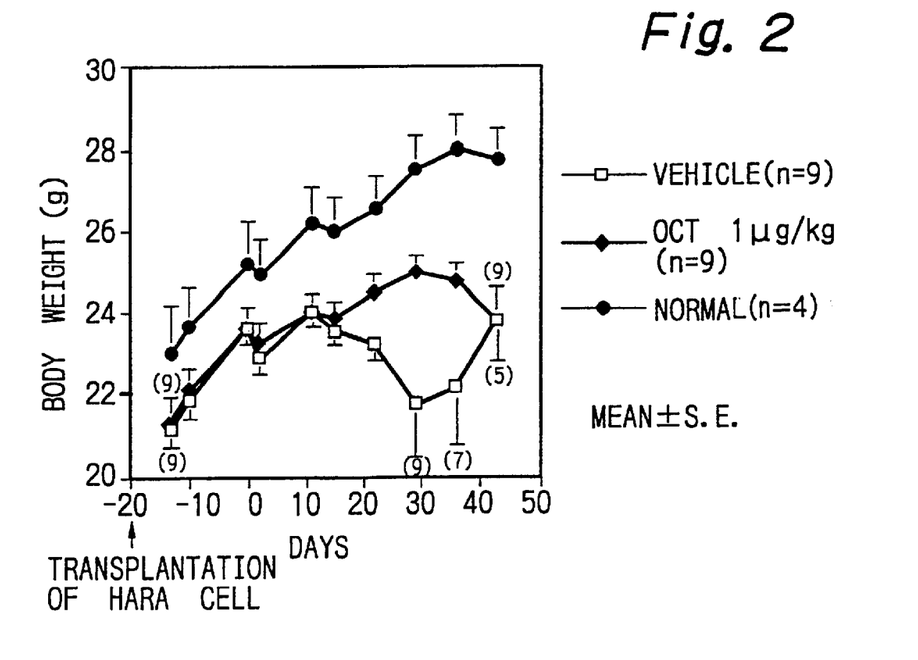
FIG. 2 shows body weight changes of bone metastasis model mice.

FIG. 2 shows changes in body weight of the tested animals. The body weights of the tested animals of the vehicle group (n=9) changed from 23.60±1.08 g on the first day of the test to 23.20±1.10 g after 15 doses on the 22nd day after starting the test, and then 21.78±3.87 g after 20 doses on the 29th day after starting the test. In contrast, the group treated with 1 μg/kg of OCT (n=9) showed body weights of 23.61±1.57, 24.51±1.27 and 25.00±1.20 g, respectively, indicating that OCT significantly suppressed body weight decrease on the 29th day ($p<0.05$). Age-matched normal mice with no Hara cells transplanted (normal in FIG. 2; n=4) showed body weights of 25.19±2.08, 26.53±1.60 and 27.50±1.66 g, respectively.

Figure 3:
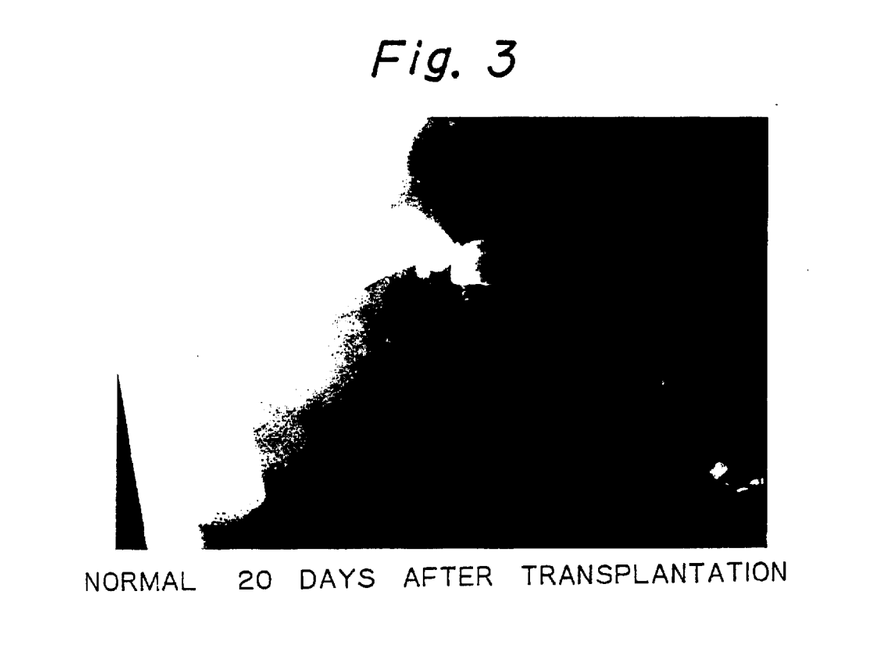
FIG. 3 is a soft X-ray photograph showing an age-matched normal mouse (normal) on the first day of the malignant tumor metastasis inhibitory experiment of Example 1.
Figure 4:
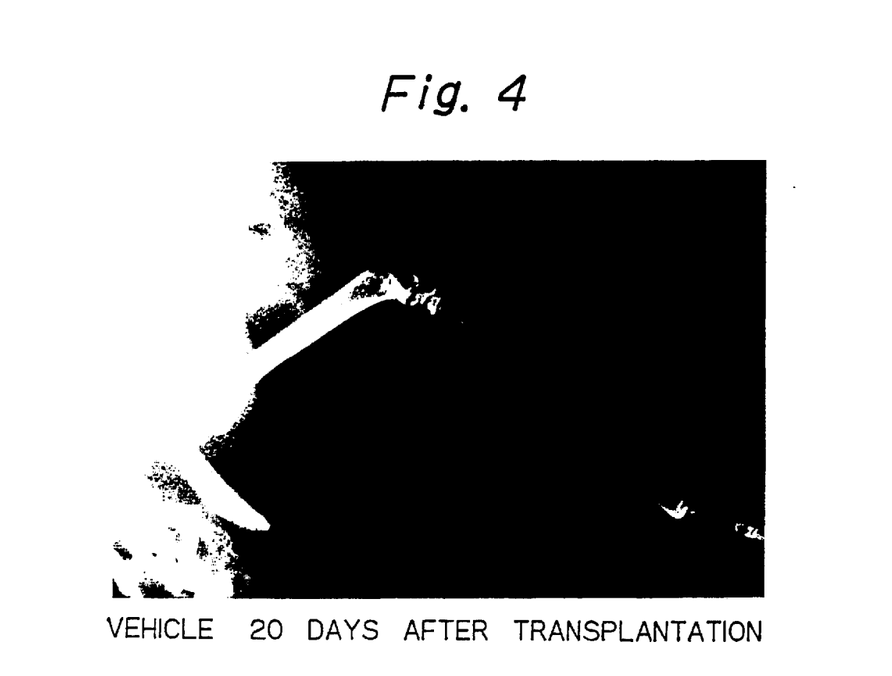
FIG. 4 is a soft X-ray photograph showing a vehicle-treated mouse on the first day of the malignant tumor metastasis inhibitory experiment of Example 1.
Figure 5:
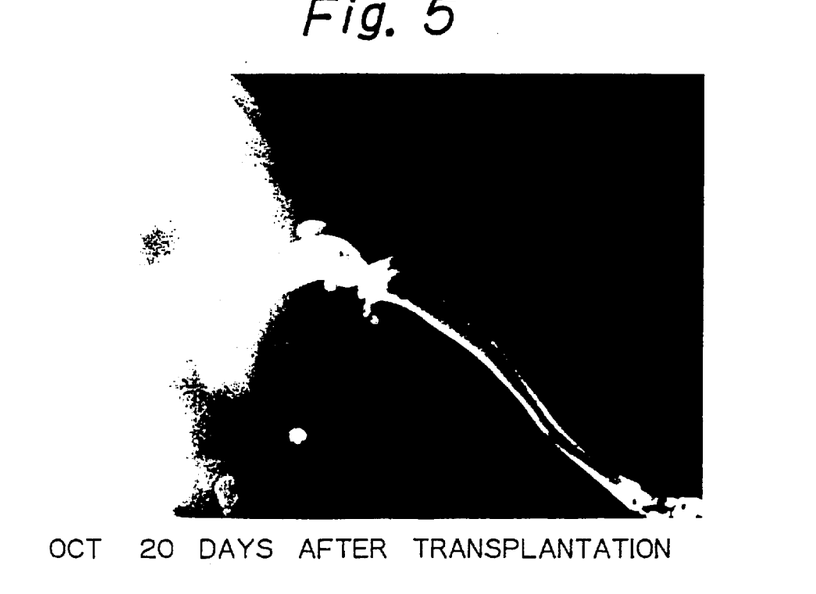
FIG. 5 is a soft X-ray photograph showing an OCT 1 (g/kg-treated mouse on the first day of the malignant tumor metastasis inhibitory experiment of Example 1.
Figure 6:
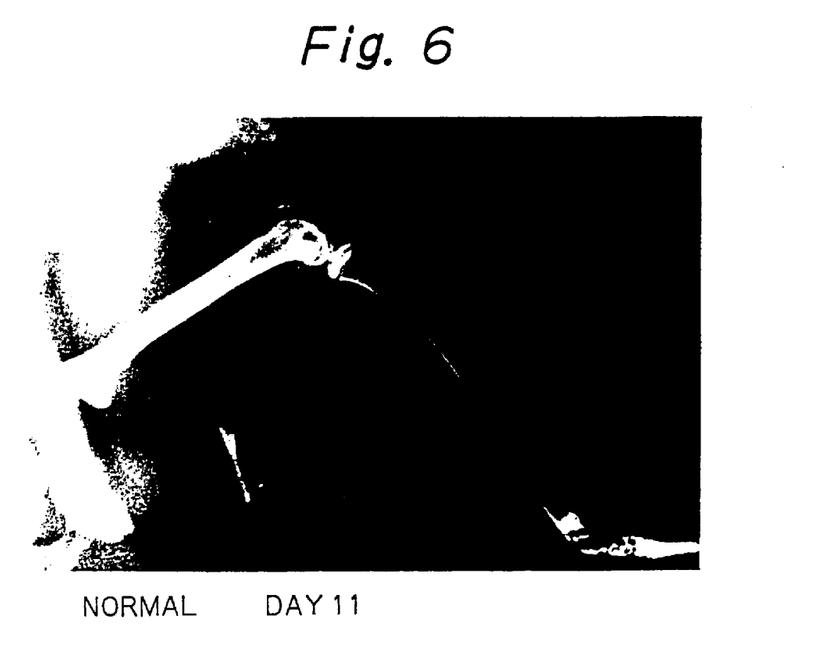
FIG. 6 is a soft X-ray photograph showing an age-matched normal mouse (normal) on the 11th day after starting the malignant tumor metastasis inhibitory experiment of Example 1.
Figure 7:
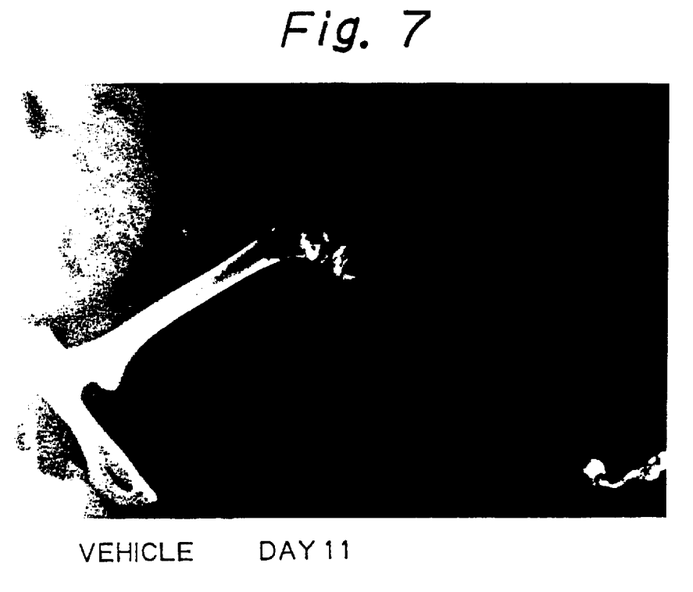
FIG. 7 is a soft X-ray photograph showing a vehicle-treated mouse on the 11th day after starting the malignant tumor metastasis inhibitory experiment of Example 1.
Figure 8:
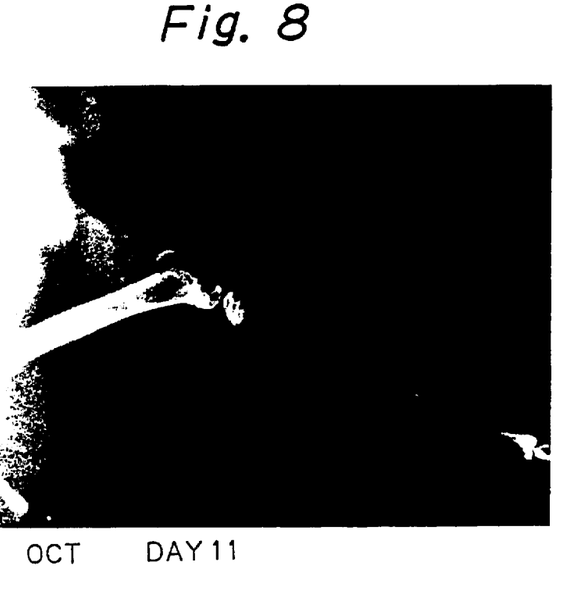
FIG. 8 is a soft X-ray photograph showing an OCT 1 (g/kg-treated mouse on the 11th day after starting the malignant tumor metastasis inhibitory experiment of Example 1.
Figure 9:
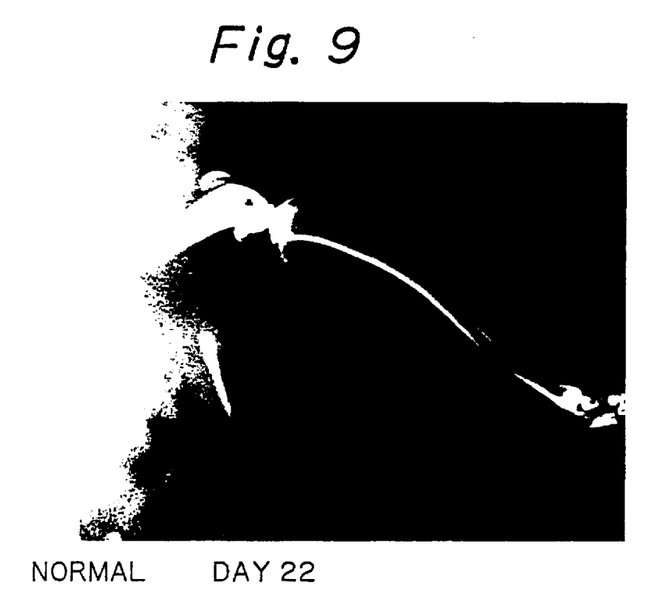
FIG. 9 is a soft X-ray photograph showing an age-matched normal mouse (normal) on the 22nd day after starting the malignant tumor metastasis inhibitory experiment of Example 1.
Figure 10:
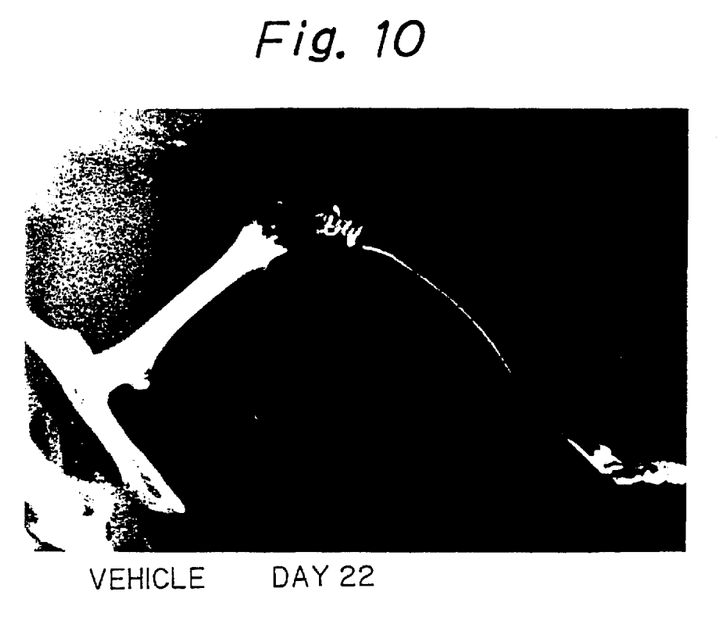
FIG. 10 is a soft X-ray photograph showing a vehicle-treated mouse on the 22nd day after starting the malignant tumor metastasis inhibitory experiment of Example 1.
Figure 11:
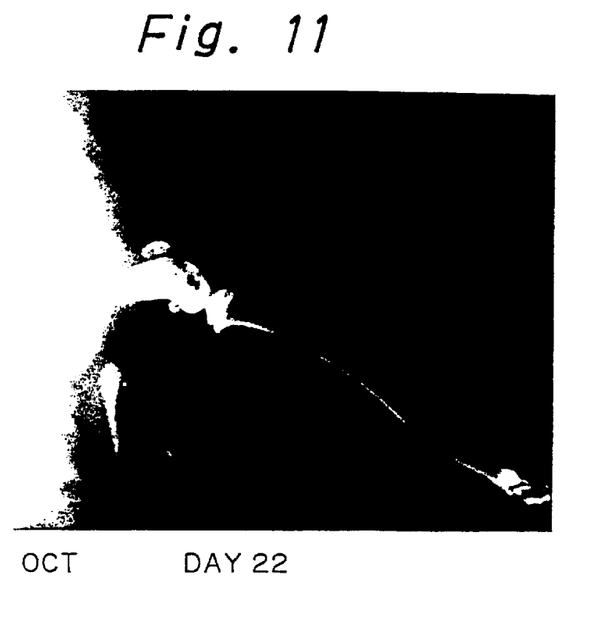
FIG. 11 is a soft X-ray photograph showing an OCT 1 (g/kg-treated mouse on the 22nd day after starting the malignant tumor metastasis inhibitory experiment of Example 1.
Figure 12:
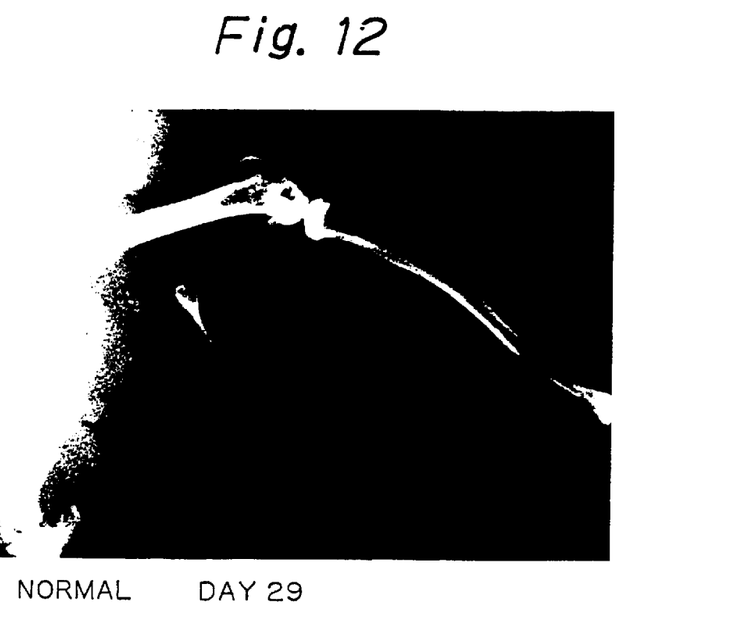
FIG. 12 is a soft X-ray photograph showing an age-matched normal mouse (normal) on the 29th day after starting the malignant tumor metastasis inhibitory experiment of Example 1.
Figure 13:
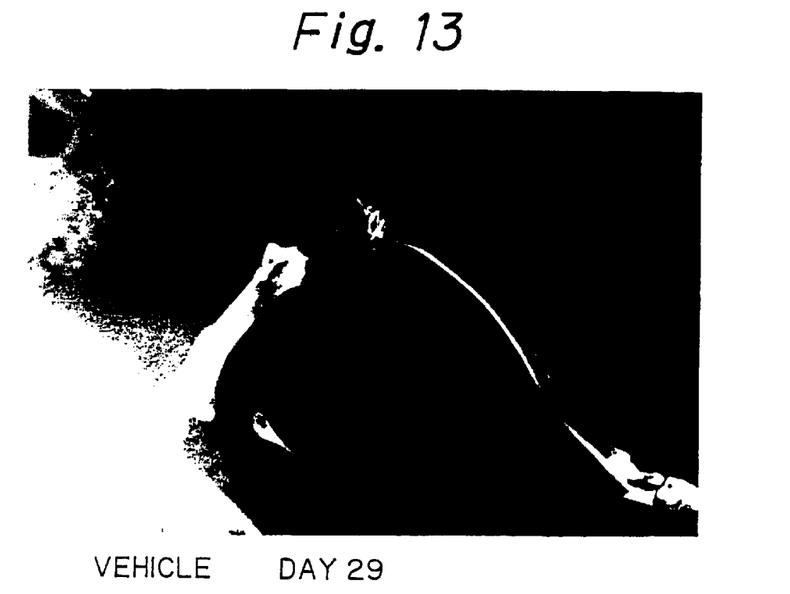
FIG. 13 is a soft X-ray photograph showing a vehicle-treated mouse on the 29th day after starting the malignant tumor metastasis inhibitory experiment of Example 1.
Figure 14:
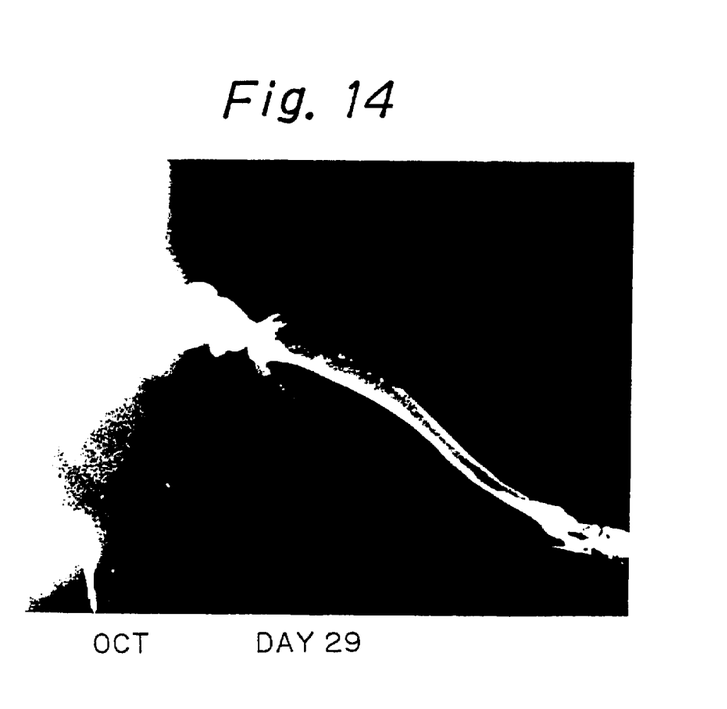
FIG. 14 is a soft X-ray photograph showing an OCT 1 (g/kg-treated mouse on the 29th day after starting the malignant tumor metastasis inhibitory experiment of Example 1.

FIGS. 3 to 14 are soft X-ray photographs of the left crus bone of one individual from each group of tested animals, i.e. age-matched normal mice (normal), vehicle-treated mice and OCT 1 μg/kg-treated mice. FIGS. 3 to 5 are soft X-ray photographs for these individuals in this order on the first day of the test, FIGS. 6 to 8 on the 11th day, FIGS. 9 to 11 on the 22nd day and FIGS. 12 to 14 on the 29th day after starting the test, respectively. Accordingly, soft X-ray photographs showing changes with time for the same individual are given in FIGS. 3, 6, 9 and 12 for a normal mouse, FIGS. 4, 7, 10 and 13 for a vehicle-treated mouse, and FIGS. 5, 8, 11 and 14 for a mouse treated with 1 μg/kg of OCT, respectively.

From these soft X-ray photographs of tested animals, no metastasis image was observed in any individual on the first day of the test. However, a clear bone metastasis was observed in one animal of the vehicle group on and after the 11th day after starting the test as evidenced from a shadow which appeared in the left curs bone in FIGS. 7, 10 and 13, and also observed in another animal on the 29th day after starting the test. These animals both died by the 32nd day after starting the test. A metastasis image was observed in further two animals, i.e. four animals in total, by the end of the test and all of them died by the 42nd day after starting the test. In contrast, no bone metastasis image was observed during the administration period and no death was observed in the group treated with 1 μg/kg of OCT.

INDUSTRIAL APPLICABILITY

The pharmaceutical agents containing vitamin D derivatives according to the present invention are useful as malignant tumor metastasis inhibitors without any especially strong side effects.

What is claimed is:

1. A method for inhibiting bone metastasis of a malignant lung tumor in a patient who has a lung cancer comprising administering to said patient an effective amount of a compound of the formula (III):

(III)

wherein $R_2$ represents a $C_1$–$C_{10}$ alkyl group substituted by one or more hydroxyl groups.

2. The method according to claim 1 wherein said compound is represented by the formula (IV):

(IV)

3. The method according to claim 2 wherein said effective amount is 1 to 20 μm per day.

* * * * *

UNITED STATES PATENT AND TRADEMARK OFFICE
CERTIFICATE OF CORRECTION

PATENT NO. : 6,869,940 B2 Page 1 of 1
APPLICATION NO. : 10/135846
DATED : March 22, 2005
INVENTOR(S) : Ogata et al.

It is certified that error appears in the above-identified patent and that said Letters Patent is hereby corrected as shown below:

On the cover, in the section (*), below the Notice insert --This patent is subject to a terminal disclaimer. --

Signed and Sealed this

Sixth Day of November, 2007

JON W. DUDAS
*Director of the United States Patent and Trademark Office*